United States Patent
Jung et al.

(10) Patent No.: US 6,573,371 B2
(45) Date of Patent: Jun. 3, 2003

(54) CELL GROWTH INHIBITING AND CELL DIFFERENTIATION SPECIFIC SYG972 GENE, GENOMIC DNA AND PROMOTER THEREOF

(75) Inventors: Neon-Cheol Jung, Taejon (KR); Jin-Man Kim, Taejon (KR); Seung-Suh Hong, Taejon (KR); Hyun-Soo Lee, Seoul (KR); Young-Rim Seong, Taejon (KR); Jae-Ho Lee, Taejon (KR)

(73) Assignee: Samyang Genex Corporation, Seoul (KR)

( * ) Notice: Subject to any disclaimer, the term of this patent is extended or adjusted under 35 U.S.C. 154(b) by 5 days.

(21) Appl. No.: 09/879,833

(22) Filed: Jun. 12, 2001

(65) Prior Publication Data

US 2002/0055107 A1 May 9, 2002

Related U.S. Application Data

(63) Continuation of application No. PCT/KR99/00756, filed on Dec. 9, 1999.

(30) Foreign Application Priority Data

Dec. 12, 1998 (KR) .......................... 1998-54933
Dec. 30, 1998 (KR) .......................... 1998-63958

(51) Int. Cl.$^7$ .......................... C07H 21/02; C07H 21/04
(52) U.S. Cl. .................... 536/23.5; 536/23.1; 536/24.1; 536/24.31; 536/24.33
(58) Field of Search ................... 435/6, 91.2; 536/23.1, 536/23.5, 24.1, 24.31, 24.33

(56) References Cited

U.S. PATENT DOCUMENTS 6,027,914 A * 2/2000 Smith et al. ............... 435/69.1

FOREIGN PATENT DOCUMENTS

| EP | 0 787 798 A2 | 8/1997 |
| WO | WO 94/11533 | 5/1994 |
| WO | WO 96/39427 | 12/1996 |

OTHER PUBLICATIONS

Adams et al. NCBI Database. National Libary of Medicine, National Institutes of Health (Bethesda, MD, USA) Accession No. AQ042423, Jul. 1998.*

Strausberg. NCBI Database. National Library of Medicine. National Institutes of Health (Bethesda, MD, USA) Accession No. AI870014, Jul. 1999.*

Fornace Jr. et al., *Annu Rev. Genet*, 1992, 26:505–24.

Takekawa et al., *Cell*, 1998, vol. 95, 521–530.

* cited by examiner

Primary Examiner—Carla J. Myers
(74) Attorney, Agent, or Firm—Darby & Darby

(57) ABSTRACT

The present invention relates to a diagnosis method of cancer using SYG972 gene and to the genomic DNA and to a promoter regulating transcription of the gene. Expression of SYG972 gene is greatly reduced in breast cancer cells compared to normal breast cells. Therefore the present invention provides a method of diagnosis method by using the gene of the present invention or its fragments as a probe. SYG972 genomic according to the present invention is composed of 4 exons and 3 introns. Promoter is 3 kb long from the transcription initiating site in the 5' direction. SYG972 genomic DNA and promoter can be used to design and screen drugs to promote or to inhibit apoptosis and differentiation of cells, especially to screen drugs to treat cancer, a disease wherein cell growth and differentiation is abnormal.

2 Claims, 5 Drawing Sheets

1. Heart
2. Brain
3. Placenta
4. Lung
5. Liver
6. Skeletal muscle
7. Kidney
8. Pancreas
9. Stomach
10. Thyroid
11. Spinal cord
12. Lymph node
13. Trachea
14. Adrenal gland
15. Bone marrow
16. Spleen
17. Thymus
18. Prostate
19. Testis
20. Ovary
21. Small intestine
22. Colon
23. Peripheral blood leukocyte 0h 4h 8h 24h 48h 1wk 0h 24h 48h 72h 0h 24h 48h 72h 1wk

SEQUENCE LISTING

<160> NUMBER OF SEQ ID NOS: 3

<210> SEQ ID NO 1
<211> LENGTH: 1066
<212> TYPE: DNA
<213> ORGANISM: HL60 cell line

<400> SEQUENCE: 1

```
gtgggtgcgc cgtgctgagc tctggctgtc agtgtgttcg cccgcgtccc ctccgcgctc      60
tccgcttgtg gataactagc tgctggttga tcgcactatg actctggaag aagtccgcgg     120
ccaggacaca gttccggaaa gcacagccag gatgcagggt gccgggaaag cgctgcatga     180
gttgctgctg tcggcgcagc gtcagggctg cctcactgcc ggcgtctacg agtcagccaa     240
agtcttgaac gtggaccccg acaatgtgac cttctgtgtg ctggctgcgg gtgaggagga     300
cgagggcgac atcgcgctgc agatccattt tacgctgatc caggctttct gctgcgagaa     360
cgacatcgac atagtgcgcg tgggcgatgt gcagcggctg gcggctatcg tgggcgccgg     420
cgaggaggcg ggtgcgccgg gcgacctgca ctgcatcctc atttcgaacc caacgagga     480
cgcctggaag gatcccgcct tggagaagct cagcctgttt tgcgaggaga gccgcagcgt     540
taacgactgg gtgcccagca tcaccctccc cgagtgacag cccggcgggg accttggtct     600
gatcgacgtg gtgacgcccc ggggcgccta gagcgcggct ggctctgtgg aggggccctc     660
cgagggtgcc cgagtgcggc gtggagactg gcaggcgggg ggggcgcctg gagagcgagg     720
aggcgcggcc tcccgaggag gggcccggtg gcggcagggc caggctggtc cgagctgagg     780
actctgcaag tgtctggagc ggctgctcgc ccaggaaggc ctaggctagg acgttggcct     840
cagggccagg aaggacagac tggccgggca ggcgtgactc agcagcctgc gctcggcagg     900
aaggagcggc gccctggact tggtacagtt tcaggagcgt gaaggactta accgactgcc     960
gctgcttttt caaaacggat ccgggcaatg cttcgttttc taaaggatgc tgctgttgaa    1020
gctttgaatt ttacaataaa cttttttgaaa caaaaaaaaa aaaaaa                  1066
```

<210> SEQ ID NO 2
<211> LENGTH: 160
<212> TYPE: PRT
<213> ORGANISM: HL60 cell line

<400> SEQUENCE: 2

```
Met Thr Leu Glu Glu Val Arg Gly Gln Asp Thr Val Pro Glu Ser Thr
  1               5                  10                  15

Ala Arg Met Gln Gly Ala Gly Lys Ala Leu His Glu Leu Leu Leu Ser
             20                  25                  30

Ala Gln Arg Gln Gly Cys Leu Thr Ala Gly Val Tyr Glu Ser Ala Lys
         35                  40                  45

Val Leu Asn Val Asp Pro Asp Asn Val Arg Phe Cys Val Leu Ala Ala
     50                  55                  60

Gly Glu Glu Val Glu Gly Asp Ile Ala Leu Gln Ile His Phe Thr Leu
 65                  70                  75                  80
```

```
Ile Gln Ala Phe Cys Cys Glu Asn Asp Ile Asp Ile Val Arg Val Gly
                85                  90                  95

Asp Val Gln Arg Leu Ala Ala Ile Val Gly Ala Gly Glu Glu Ala Gly
            100                 105                 110

Ala Pro Gly Asp Leu His Cys Ile Leu Ile Ser Asn Pro Asn Glu Asp
            115                 120                 125

Ala Trp Lys Asp Pro Ala Leu Glu Lys Leu Ser Leu Phe Cys Glu Glu
            130                 135                 140

Ser Arg Ser Val Asn Asp Trp Val Pro Ser Ile Thr Leu Pro Glu Arg
145                 150                 155                 160

<210> SEQ ID NO 3
<211> LENGTH: 4444
<212> TYPE: DNA
<213> ORGANISM: HL60 cell line

<400> SEQUENCE: 3
gatcctcaaa cttctagtgg gcattgccca ctcctcaaca caggggcatc ccaggcccag     60
aagcttcagc atgtgtctga actgaagggt ggtggtgggt ctgctggaag gccacctttg    120
cctgcagaca aaattgttct cccaattga  gatgggggct ttggggccat gggactgac     180 ataacaaagc aaagtgaggc tgtatcatat gtcaaaaagg cagtttcctg aaattgaata    240
ctttaaaaat gtgagcagag tagaacagcc cagggggtcg tcaatcatct cttctggtcc    300
aggctagctc aggagggact ggaaatgcac cacccccaa  ctcgaagccg ggagtgttca    360
ttagtggcct tcctctcgga ggaggggctg aggcttcagg cctagccttt gttttctctg    420
gcctggcatg taggcagatt tttagcgtca taaattggag aggtgggtgc tagcatgtta    480
agtaaatctt atttccagca tgtcctgggg acctgggact aatacatttt aagaaatgtt    540
taatagtagg ccgggtgcgg ttgctcatgc ctgtaatccc agcactttgg gaggccgagg    600
tgggtggatc acgaggtcag gagtttgaga ccagcctggc caacatggtg aaactctgtt    660
tctactaaaa atacaaaaat tagcccggcg tggtggcgca cctgtagtcc cagctactcg    720
ggaggctgaa gcagaaggat cgcttgaacc cgggaggcgg aggttgcagt gagccgagat    780
tgtgccaccg cactccagcc tgggcaaccg agcgagactc cgtctcaaaa agaaaagaa    840 aagaaaagaa aagtttaata gttttaaaag agtaataacct atattccaat cacttaaaat    900
taacatattt tatccaatca aggcatatca tcattttata catcaagaaa gaaagaaac    960 tagcgaacaa acgggggcata atgccgcctg gctccgcttc ccctcccct  ctcccccgt   1020 ccttaggaga cacctctgga gttcagaaat gctaggagag caagctcttc attcttagaa   1080
tccaggaagg gccgggcttt tgcagctctc ctctgccagg aagccgctgg ggggcgcaag   1140
acgccagctt ctcaccttgg cagaagtgcc tgcctgcaag cgcagaatgg aaacttcccc   1200
ataacaaatt cagaagtacc ttgtacattc accacccacc tgaagaaagc ctgaatgaaa   1260
ggaacaaagc cacggcgttg tttactttcc cattatcgcc ccagtcttgc ggcagggccc   1320
gggtttccat ccaatccacc cggcccgcca ctgtcctggc cagtctccaa ggcttcaccc   1380
aaaaaaagga agcaatgagg tgtcccccag cgcgccttt  cacgtagcac agaaggtgct   1440
cagtgggtga atcctctgaa agtgccagcg tgtatggtca acggcagca  acctctagcc   1500 tattaaactc tcccaagatc tcttccgac  ttattccatt gccggaaaaa aggcttttta   1560
catatgcgca tttaagtaat taagatattt caacatggta taagacgtag gggctcttac   1620
tccatcagta ctggatggga atttcctttt gccctctact ccccagggta actgcagtcc   1680
```

-continued

```
cacctgaatg cgttttgcag cccttactcg ggttctattt atgcgcagct tggacagggc    1740
tcactgggcc cggccgggca gctccgtggc cgtccctctc caccgccctt cccccgcgcc    1800
aggccaatgc aagggtgtgt gtgttggggg gaggggagga caaaagggt tcaggatctt     1860 tttaacctgc ctgcagatgg cgccccggga aagattccga gctgcattac ctaagctcca    1920
ggggctgcag ccgcggggtc ccggccacag ggcgtccagc cgcgaagact gcacagcagc    1980
tctccgtcct tcccaactcg cgcggctgtt cggcacccgt gcgaggaacg gatggaaggg    2040
aattacttgt agcagggcca gtactggggg cgtgcactca gggaccacgg agtggcactc    2100
agcctcgacc ccacgcgcca ggcagcccgg cgaccccac gcgcggcggg gtcctgccca     2160
ccccacccgg cggcaggtgg acagtgttgc tatgaagaga aagcctcgat tgtccctaca    2220
gcaaaccgcc acacgccaga cctctgctat tgtgcgccct ccatagaaat gcaaacgagc    2280
gcgtgcgccg ccgcaatct gctcgtcccc gcccgccccc gtctcccgcg ccccgccgcg     2340
ctcggccaag ggcggggagg tggggtggga tcttccagag acggctcaat gtacacattg    2400
agtatgcctg gcaggcatca ccagcgcgct cgggacgcta gtggtcagct gcaggggggct   2460 gtgcccactg cctttttgcaa gcctctaact ggcgctacct gttttttacct taatttctgg  2520 ctccaatgca acagtctcat agacttcaaa ttaaagaaaa gaaacaaata gaaaggtagc    2580
aatacaaaat gcaaaaaaaa atcccttttgc ctctataaag gtgcttttcg caaattgcag   2640
catcatataa gcaaacaagg ttttgtggg ttgggttttt tctttttttt ttttttttac     2700
tttttccttt taaggacttc aaaaaaaaaa aaaagccagg cgagatgaaa tctgcaggct    2760
ccagtctgcc tggtaacacc ccaacaaaag cggcagattt gaggcattgt catcccccgc    2820
acccctcccc acgtggcctt ctggcagcag ccgctggctc gccgcctcat ttacatcaga    2880
aagcgggtgc cggccaatag gcgcgcagcc tcgcgcagc tggcggcgcc gcacccacca    2940
gcctatataa gggcgcgcag cgtagtaggg gcgcactcgc tggtggtggg cgcgccgtgc    3000
tgagctctgg ctgtcagtgt gttcgcccgc gtcccctccg cgctctccgc ttgtggataa    3060
ctagctgctg gttgatcgca ctatgactct ggaagaagtc cgcggccagg acacagttcc    3120
ggaaagcaca gccaggtggg tttcaggcg ctgagaaagc cgctggtcgg tcggcgaccg     3180
tcagggtttt ccaggtgggg aatccgcggg gtaggagggg agcgcggggg tccgggcgcc    3240
agatcccggt tggagagccg gggtgcaggc gctgagccgg gattggagtg tggttggagt    3300
tggggagcca agggtgtgtg ccgtggccg gggctgggt ctccgccgcg ccctccggcc      3360
ggctcccgct cactgcgctg gctcctccgc aggatgcagg gtgccgggaa agcgctgcat    3420
gagttgctgc tgtcggcgca gcgtcaggc tgcctcactg ccgcgtcta cgagtcagcc     3480 aaagtcttga acgtgtaagt gtagacgcgg cccaggctgg gagacagggg cggggtgaa    3540 tggcgaggag actggcggat gggaggggtg gcggcggag aactcggcta gccggttctg     3600
acctaggtcc ccgccttgcc ctcgcaggga ccccgacaat gtgaccttct gtgtgctggc    3660
tgcgggtgag gaggacgagg gcgacatcgc gctgcagatc cattttacgc tgatccaggc    3720
tttctgctgc gagaacgaca tcgacatagt gcgcgtgggc gatgtgcagc ggctggcggc    3780
tatcgtgggc gccggcgagg aggcgggtgc gccgggcgac ctgcactgca tcctcatttc    3840
ggtgagtaca gtcccgtcct gtccccgccc cagtgtcgtt cccgcctcgg cccgcggcca    3900
gccaggctga ccctgctctc tctccgcaga acccaacga ggacgcctgg aaggatcccg     3960
ccttggagaa gctcagcctg ttttgcgagg agagccgcag cgttaacgac tgggtgccca    4020
```

-continued

```
gcatcaccct ccccgagtga cagcccggcg gggaccttgg tctgatcgac gtggtgacgc    4080
cccggggcgc ctagagcgcg gctggctctg tggaggggcc ctccgagggt gcccgagtgc    4140
ggcgtggaga ctggcaggcg ggggggcgc ctggagagcg aggaggcgcg gcctcccgag     4200
gaggggcccg gtggcggcag ggccaggctg gtccgagctg aggactctgc aagtgtctgg    4260
agcggctgct cgcccaggaa ggcctaggct aggacgttgg cctcagggcc aggaaggaca    4320
gactggccgg gcaggcgtga ctcagcagcc tgcgctcggc aggaaggagc ggcgccctgg    4380
acttggtaca gttgcaggag cgtgaaggac ttagccgact gcgctgcttt ttcaaaacgg    4440
atcc                                                                 4444
```

CELL GROWTH INHIBITING AND CELL DIFFERENTIATION SPECIFIC SYG972 GENE, GENOMIC DNA AND PROMOTER THEREOF This is a continuation of International Application Serial No. PCT/KR99/00756, filed Dec. 9, 1999, the entire disclosure of which is hereby incorporated by reference.

TECHNICAL FIELD AND BACKGROUND ART

The present invention relates to a gene relating to cell differentiation (SYG972), amino acid sequence coded therefrom and their application to cancer diagnosis. The present invention also relates to a genomic DNA of SYG972 and to a new promoter.

Cell differentiation is the series of events involved in the development of a specialized cell having specific structure, functional, and biochemical properties. Cell differentiation occurs mainly at the time of fetus formation, but also occurs through out the entire life. Differentiating cells receive specific intracellular signals to participate in cell differentiation according to its program. During this process, expression of many different genes is regulated through a complex path. Genes that regulate cell differentiation are known to encode transcription-regulating factors including homeoproteins and cell cycle proteins. Most of the cell differentiation related genes, however, act on specific cell lines in a specific mode. Nevertheless, a common phenomenon relating to differentiation, that is, differentiation accompanying growth inhibition indicates that there exists a key regulator for cell differentiation. Accordingly, it is necessary to separate the functioning gene and elucidate its function.

One of the most prominent characteristics of cancer cells compared to normal cells is that cancer cells can amplify indefinitely. In order for normal cells to mutate to into cancer cells, the intracellular growth inhibiting genes must be deactivated. One of the representative example is the deactivation of the P53 gene that is found frequently in cancer cells. The product of the P53 genes is intra-nuclear transcription regulating factor for the normal cells, but mutation in this gene results in abnormal growth of the cells and which became cancer cells.

An example of a cancer regression gene closely related to cell differentiation is an erbA gene encoding thyroid hormone receptor. When red blood cell precursor cells are infected with an avian erythroblastosis virus, and the function of the erbA gene is regulated abnormally, this cell differentiates not into red blood cell but into undifferentiated immortalized cancer cells. In other words, generation and progress of cancer cells are complex phenomena that accompany expression of many genes and also accompanies the blocking of cell differentiation. Therefore, it is very important to find factors regulating cell differentiation and growth inhibition in diagnosing and treating cancers.

Promoters, sites regulating the transcription of a gene, are generally located at 5' position of transcription start site. Gene expression is regulated depending on the transcription factor that binds this domain. In other words, the promoter of the gene determines regulation site for tissue specificity of a specific gene and changes in the expression according to the differentiation. Therefore, cloning a gene promoter and determining the sequence are very important in studying gene expression mechanism and finding gene expression regulating factors.

DISCLOSURE OF THE INVENTION

It is an object of the present invention to provide a cancer diagnosis method using SYG972 gene, its fragment and polypeptide derived therefrom.

It is another object of the present invention to provide a genomic DNA of SYG972.

Another object of the present invention is to provide a sequence for a new promoter.

Another object of the present invention is to provide a method to design and screen drugs by using a promoter of SYG972.

DETAILED DESCRIPTION OF THE INVENTION

Figure 1:
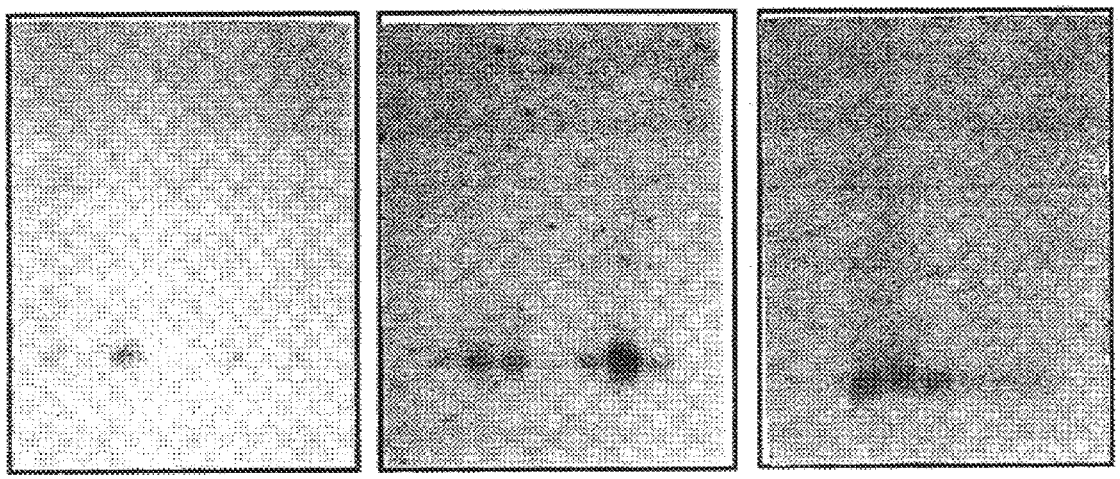
FIG. 1 is a Northern blot showing an expression of SYG972 mRNA in human tissue.

Terminology and techniques in the present application have the meanings that are generally used in the field of the present invention, unless otherwise specified. Also the references mentioned in the present application are the references which further explain the present invention and are incorporated by reference in the present application.

"Amino acid sequence", "polypeptide" or "protein" is not limited to the perfectly natural amino acid sequence.

"Sequence mutant" refers to an altered sequence due to substitution, deletion or addition of one or more bases in SYG972 and SYG 972 genomic DNA while maintaining a biological or immunological activity.

"Amino acid mutant" refers to an altered amino acid sequence due to substitution, deletion or addition of one or more amino acids derived from SYG972 while maintaining a biological or immunological activity.

"SYG972 derivative" refers to a gene wherein one or more of the base of SYG972 are altered while maintaining the biological characteristic of the protein that it encodes.

The present inventors have separated gene SYG972 using HL60 cell line as a model system. This cell line shows histo-pathological reading of acute promyelocytic leukemia, and especially has characteristics of differentiation by addition of various foreign factors such as TPA, DMSO and retinoic acid.

To isolate SYG972, mRNA was extracted from untreated HL60 cells and HL60 cells differentiated with TPA. cDNA was isolated by subtraction hybridization (Fornace, A. J. (1988). DNA damage-inducible transcripts in mammalian cells. *Proc. Natl. Acad. Sci USA* 85, 8800–8804) and the resulted cDNA clone was identified by Northern blot and then isolated a gene that increases in the HL60 differentiation model. The sequence of SYG972 gene is listed as Sequence No. 1.

The database search based on the homology of the gene sequence resulted in two similar genes, Gadd45 and Myd118. Expression of Gadd45 (Growth Arrest and DNA Damaging inducible gene) increases upon X-ray or ultraviolet radiation or upon treatment with alkylating agent. Gadd45 has a characteristic of responding to DNA damaging (Fornace, A. J. (1988). DNA damage-inducible transcripts in mammalian cells. Proc Natl. Acad. Sci USA 85, 8800–8804). Myd118 is a gene that increases upon Myeloid cell differentiation (Abdollahi, A. (1991). Sequence and expression of a cDNA encoding Myd118: a novel myeloid differentiation primary response gene induced by multiple cytokines. Oncogene 6, 165–17).

In spite of the homology among these genes, gene expression of SYG972 in the tissue is totally different with known Gadd45 or Myd118. Expression of Gadd45 or Myd118 is transiently increased by specific stimuli such as Myeloid cell differentiation or DNA damaging. On the other hand, SYG972 shows high expression rate in a variety of tissues. Therefore, SYG972 probably has an important role in the function of many different tissues in the absence of foreign stimuli.

In order to examine the function of SYG972 on cell differentiation, the expression behavior of SYG972 gene was investigated by a well-established differentiation model of various cells, and this investigation revealed that SYG972 increases upon the initiation of differentiation in PC12 cell line that differentiates into nerve cells and in C2C12 and L6 that differentiate to muscle cells.

Expression of SYG972 was observed in the heart, placenta, skeletal muscle, pancreas, gastrointestinal tract, thyroid, spinal cord, lymph node, trachea, adrenal, bone marrow, prostrate, testis, ovary, small and large intestines. Among these, higher level of SYG972 expression was observed in the placenta, adrenal, testis and ovary. One thing to note is that the organs, in which the over expression was observed, are mostly mesoderms that have the same genetic origin. Especially all of these organs function as steroid hormone synthesis and secretion. These facts indicate that SYG972 has an important role in a developing embryo, especially in the formation of mesodermal organs.

The amino acid sequence induced from SYG972 sequence is listed in Sequence No. 2.

The present invention relates to a cancer diagnosis method using a DNA having a sequence selected from the group consisting of Sequence 1, its fragment, its mutant, its derivatives, their fragments, and their allelomorphic mutant.

The present invention also relates to a cancer diagnosis method using a peptide which is coded from a DNA having a sequence selected from the group consisting of Sequence 1, its fragment, its mutant, its derivatives, their fragments, and their allelomorphic mutant or an antibody therefrom.

Expression of SYG972 gene is high in differentiated normal tissues but whereas it is inhibited upon canceration. This characteristic of SYG972 gene can be used in cancer diagnosis.

As an example, in a tissue of a breast cancer patient, mRNA of SYG972 was rarely observed around the cancer cells, but was highly expressed in the surrounding normal tissues. Especially among the cancer tissues, while a weak expression was observed at the boundary of cancer adjacent to the normal cells, there was no expression detected at the central cancer tissue. Therefore, SYG972 gene can be used as a diagnostic gene to distinguish cancer from normal cells.

As another example, SYG972 gene of the present invention is not expressed in B cells in the lymph node, but highly expressed specifically in T cells. Accordingly the SYG972 gene can be advantageously used in distinguishing B cells and T cells in searching the origin of cancer in various lymphomas.

The diagnosis method of the present invention, which is carried out with a tissue specimen isolated from a subject, can employ a well known hybridization method by using a DNA having a sequence selected from the group consisting of SYG972, its fragment, its mutant, its derivatives, their fragments and their allelomorphic mutant.

The diagnosis method of the present invention, which is carried out with a tissue specimen isolated from a subject, can employ a well known interaction method by using a peptide coded from a DNA having a sequence selected from the group consisting of SYG972, its fragment, its mutant, its derivatives, their fragments and their allelomorphic mutant, or an antibody therefrom.

The present invention relates to the genomic DNA of SYG972 gene.

SYG972 genomic DNA according to-the present invention comprises of 4 exons and 3 introns. The promoter is about 3 kb long from the transcription start site to the 5' direction.

Therefore, the present invention relates to a DNA, wherein the DNA has a sequence selected from the group consisting of:

a DNA comprising Sequence No. 3;

a fragment of a DNA having Sequence No. 3;

a mutant of a DNA having Sequence No. 3;

a derivative of a DNA having Sequence No. 3; and an allelomorphic mutant of a DNA having Sequence No. 3.

The present invention also relates to a DNA having a sequence selected from the group consisting of (a) a DNA sequence of comprising base No. 1 to 2973 of Sequence 3 or a fragment thereof; and (b) a DNA sequence capable of hybridizing to (a), wherein said DNA has a promoter activity.

The present invention relates to a method of designing and screening drugs using a SYG972 promoter.

Since SYG972 DNA plays an important role in cell differentiation, SYG972 genomic DNA and the promoter that regulates its expression can be used in designing and screening drugs that promote or inhibit cell apoptosis and differentiation. Especially these can be used as a useful tool in screening the drugs for the disease where cell differentiation and apoptosis occur abnormally, i.e., cancer, Alzheimer's disease or Parkinson's disease, and degenerative nervous diseases.

The present invention will be further illustrated by the following examples. It will be apparent to those have conventional knowledge in the field that these examples are given only to explain the present invention more clearly, but not limited to the examples given.

EXAMPLE 1

Isolation of SYG972 DNA

A HL60 cell line was cultured in RPMl (GibcoBRL) medium supplemented with 20% bovine fetal serum, 100 unit/ml penicillin G sodium and 100 μg/ml streptomycin sulfate. Differentiated H160 cells were obtained by treating $5 \times 10^{-8}$ M TPA (12-O-tetradecanoylphobol-13-acetate) in the medium for 3 days. Total RNA in the cell was isolated by an acid guanidinium thiocyanate phenol-chloroform method (Chomczynski, P., Sacchi, N. (1987)). Single-step method of RNA isolation by acid guanidinium thiocyanate phenol-chloroform extraction. (Anal. Biochem. 162, 156–159). The obtained RNA was dissolved in 20 μl sterilized distilled water for quantification by spectrophotometer and then only poly(A) DNA was isolated by oligo dT chromatography from which, a single strand cDNA was synthesized by using M-MLV reverse transcriptase. Differentiation specific cDNA was separated using hydroxyapatite chromatography. From the separated single strand cDNA, the second strand cDNA was synthesized and then cloned at EcoR I and Xho I sites of Uni-ZAP XR vector. (Schneder, C. et.al. 91988). Genes specifically expressed as growth arrest of mammalian cells. Cell 54, 787–793). Library of cloned vector was constructed by packing with packaging extract (Gigapack II packaging extract, Stratagene). Finally SYG972 gene was obtained from this library.

By determining DNA sequence, SYG972 gene was identified as 1066 bp long. Among the sequence, the open leading frame that can be translated into protein is 480 bp long (Sequence No. 1). SYG972 amino acid sequence estimated from the DNA sequence is listed as Sequence No. 2.

EXAMPLE 2

Expression Behavior of SYG972 in Human Tissue

To investigate the level of expression of SYG972 in human tissue, total RNA was extracted from human tissue and analyzed by Northern blot hybridization (Sambrook, J. et. al. (1989). Molecular cloning: a laboratory manual. Cold Spring Harbor Laboratory Press). To a membrane (Clontech) blotted with extracted RNA from human tissue, SYG972 DNA probe marked with $\alpha$-$^{32}$P-[dCTP] was hybridized and reacted for 24 hours and washed with 2×SSC, 0.1% SDS solution for 10 minutes at room temperature and for 30 minutes at 50° C. The washed membrane was exposed at −70° C. for 1 week on an x-ray film and developed. The result is shown in FIG. 1.

Expression of SYG972 varied for different tissues. Expression of SYG972 was observed in the heart, placenta, skeletal muscle, pancreas, gastrointestinal tract, thyroid, spinal cord, lymph node, trachea, adrenal, bone marrow, prostate, testis, ovary, small and large intestines. Among these, over expression was observed in the placenta, adrenal, testis and the ovary,

EXAMPLE 3

Expression Behavior of SYG972 in Various Differentiation Models

To investigate the quantitative change of SYG972 mRNA during cell differentiation, three different cell differentiation models were used. PC12 cells which are pheochromocytoma, have a characteristic of differentiating to nerve cells by NGF (nerve growth factor), and C2C12 and L6 which are mouse myoblasts and white mouse myoblast respectively, have a tendency to differentiate to muscle cells by a stimulus inducing differentiation. PC12 cells were cultured in 10% horse serum (GibcoBRL) supplemented with 5% bovine fetal serum, 100 unit/ml penicillin G sodium and 100 µg/ml streptomycin sulfate. To obtain RNA from differentiated PC12 cells, 50 ng/ml of NGF (Gibco BRL) was added in the medium. After a few hours, differentiated cell morphology was identified under microscope and collected at different time intervals.

C2C12 and L6 cells were cultured in 10% bovine fetal serum supplemented with 100 unit/ml penicillin G sodium and 100 µg/ml streptomycin sulfate. To differentiate these cells, the medium was exchanged with DMEM supplemented with 2% horse serum and 5% horse serum, respectively. After a few hours, differentiated cell morphology was identified under microscope.

Total RNA was extracted from each sample as described in Example 1. Thirty micrograms of total RNA was mixed with the same volume of RNA loading buffer (50% formamide, 6.2% formaldehyde, 20 mM MOPS (3-[N-morpholino]propanesulfonic acid), 5 mM sodium acetate, 1 mM EDTA) and denatured for 10 minutes at 65° C. All of the samples were electrophoresed in 1.2% formaldehyde gel for 1 hour at 100 V, separated RNA was transferred into Nylon membrane for 48 hours by a capillary method. The membrane was finally cross-linked using UV cross-linker (UVP500; Hoefer, 120,000 µJ/cm$^2$). To prepare SYG972 cDNA probe marked with radioisotope, SYG972 cDNA was cut from vector using EcoR I and Xba I restriction enzymes, marked with 50 µCi $\alpha$-$^{32}$P-[dCTP] per 25 ng DNA by using Radprime labeling kit (Gibco BRL), and separated by using NucTrap paobe separation column.

Figure 2A:
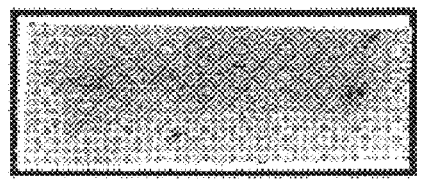
FIG. 2A is a Northern blot showing an increase of SYG972 mRNA according to the differentiation of PC12 cell to nerve cell.
Figure 2B:
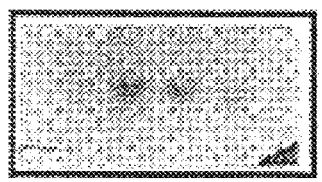
FIG. 2B is a Northern blot showing an increase of SYG972 mRNA according to the differentiation of C2C12 cell to muscle cell.
Figure 2C:
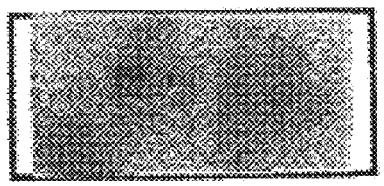
FIG. 2C is a Northern blot showing an increase of SYG972 mRNA according to the differentiation of L6 cell to muscle cell.

The Nylon column prepared-above was cultures in hybridization buffer (50% formamide, 5×SSPE, 5×Denhardt solution, 0.01% SDS, 1 mg/ml denatured salmon sperm DNA). To this, separated probe was added and hybridized for 24 hours. The membrane was washed with primary washing solution (2×SSC, 0.1% SDS) at room temperature for 10 minutes, with secondary washing solution (0.1×SSC, 0.1% SDS) for 30 minutes at 50° C., and exposed at −70° C. for 1 week on an x-ray film and developed. As shown in FIGS. 2A, 2B, and 2C, SYG972 RNA increased meaningfully as the degree of cell differentiation progressed. As PC12 differentiated to nerve cells, RNA levels increased 7 days after induction of differentiation. In the case C2C12 and L6 cells differentiated to muscle cells, large amount of RNA was found 1 day after differentiation induction.

EXAMPLE 4

Expression of SYG972 in Mouse Tissue

Figure 3:
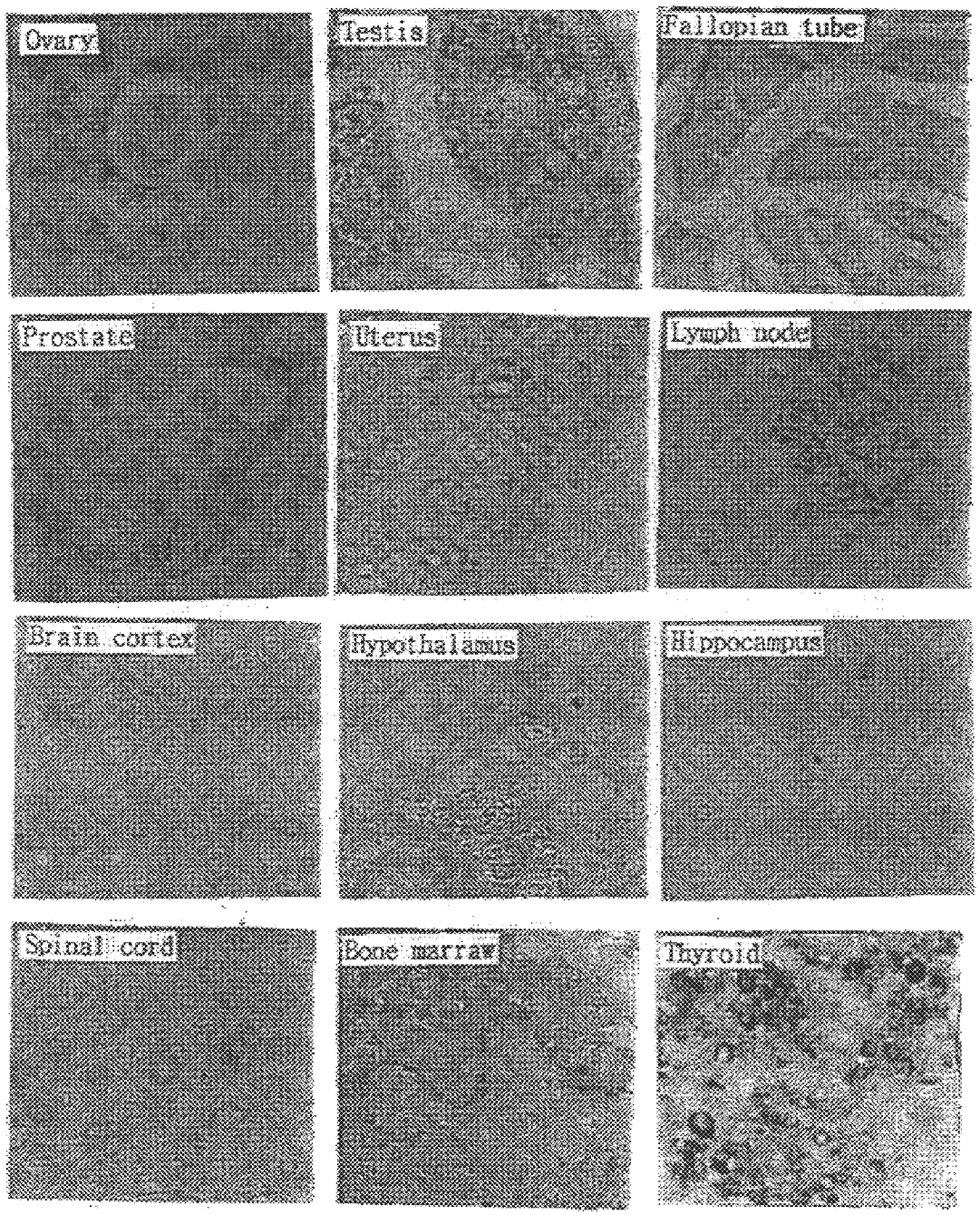
FIG. 3 is an in situ hybridization photograph showing the distribution of SYG972 in normal mouse tissue.

SYG972 gene expression level was investigated by using in situ hybridization method developed by Braissant and co-workers (Braissant, O. et. al. (1996)). Differential expression of peroxisome proliferator-activated receptors (PPARs): tissue distribution of PPAR-$\alpha$, $\beta$, and -$\gamma$ in an adult rat. Endocrinology 137, 354–366). in other words, antisense-DIG SYG972 RNA probe was prepared by cutting pBluescript II vector containing SYG972 cDNA with EcoR I and treated with DIG-11UTP. Mouse tissue specimen for analysis was obtained from anaesthetized 5 week old mouse and fixed for 24 hours in 4% formaldehyde-PBS and dehydrated continuously in 70%, 95% and 100% Xylene. Dehydrated specimen was solidified in parablast, cut in 5 µm width and adhered to ProbeOn plus slide (Fisher). Adhered specimen was hybridized with antisense probe after pre-treatment. Non-specifically bound probes were washed through post-treatment. To identify the probe in the specimen, colorization reaction was induced by using DIG specific antibody (Boeringer Mannheim) and NBT (Nitroblue tetrazolium), BCIP (5-bromo-4-chloro-3-indolylphosphate) as substrates. The tissue whose in situ hybridization is finished were observed under microscope and photographed. Representative results are shown in FIG. 3 and Table 1. DIG specific antibody attached with alkali phosphorylation enzyme used in identifying RNA marked with DIG formed dark blue precipitation with NBT and BCIP Therefore, dark blue region in the photograph is where the expression of SYG972 was high. As can be seen from FIG. 3 and Table 1, SYG 972 gene is highly expressed in luteum of the ovary, Sertoli cells and germ cells in the testis, epidermal cells of the inner layer of Fallopian tube, gland cell of the prostate and uterus, T cell in lymph node, nerve cells in the cerebrum and spinal cord, myeloid cells of the bone marrow and megakaryocyte. Especially the expression level increased as leteum developed in Follicle cells that composed of leteum in the ovary, meaning that SYG972 is related with cell differentiation as described above. In the lymph node, expression was not found in the B cell, but was high specifically in T cell. Also in the cerebrum and spinal cord, SYG972 gene was specifically expressed in the nerve cells only.

TABLE 1

| Tissue | Cell type | Degree of expression |
|---|---|---|
| Cerebrum | Cerebrum cortex nerve cell | +++ |
|  | Hippocampus nerve cell | +++ |
|  | Hypothalamus | +++ |
| Cerebellum | Purkenje cell | ++ |
| Spinal cord | Nerve cell | +++ |
| Hypophyseos |  | +++ |
| Kidney | Peroximal tubule | ++ |
|  | Distal tube | − |
| Liver | Hepatocyte | − |
| Lung | Alveolar cell | + |
| Pancreas | Acinus | − |
|  | Islet | − |
| Heart | Cardiac cell | + |
| White fat cell |  | ++ |
| Brown fat cell |  | − |
| Spleen | White pulp | ++ |
|  | Red pulp | − |
| Lymph node | T cell | +++ |
|  | B cell | − |
| Testis | Spermatogonia | +++ |
|  | Sertoli cell | +++ |
|  | Leydig cell | − |
| Ovary | Oocyte | − |
|  | Follicular cell | +++ |
|  | Luteum | +++ |
|  | White luteum | + |
| Uterus | Endometrial gland | ++ |
|  | Myometrium | − |
|  | Fallopian tube | +++ |
| Osteoid tissue | Chondrocyte | +++ |
|  | Ganglion | +++ |

EXAMPLE 5

Expression of SYG972 in Human Breast Cancer Tissue

Figure 4:
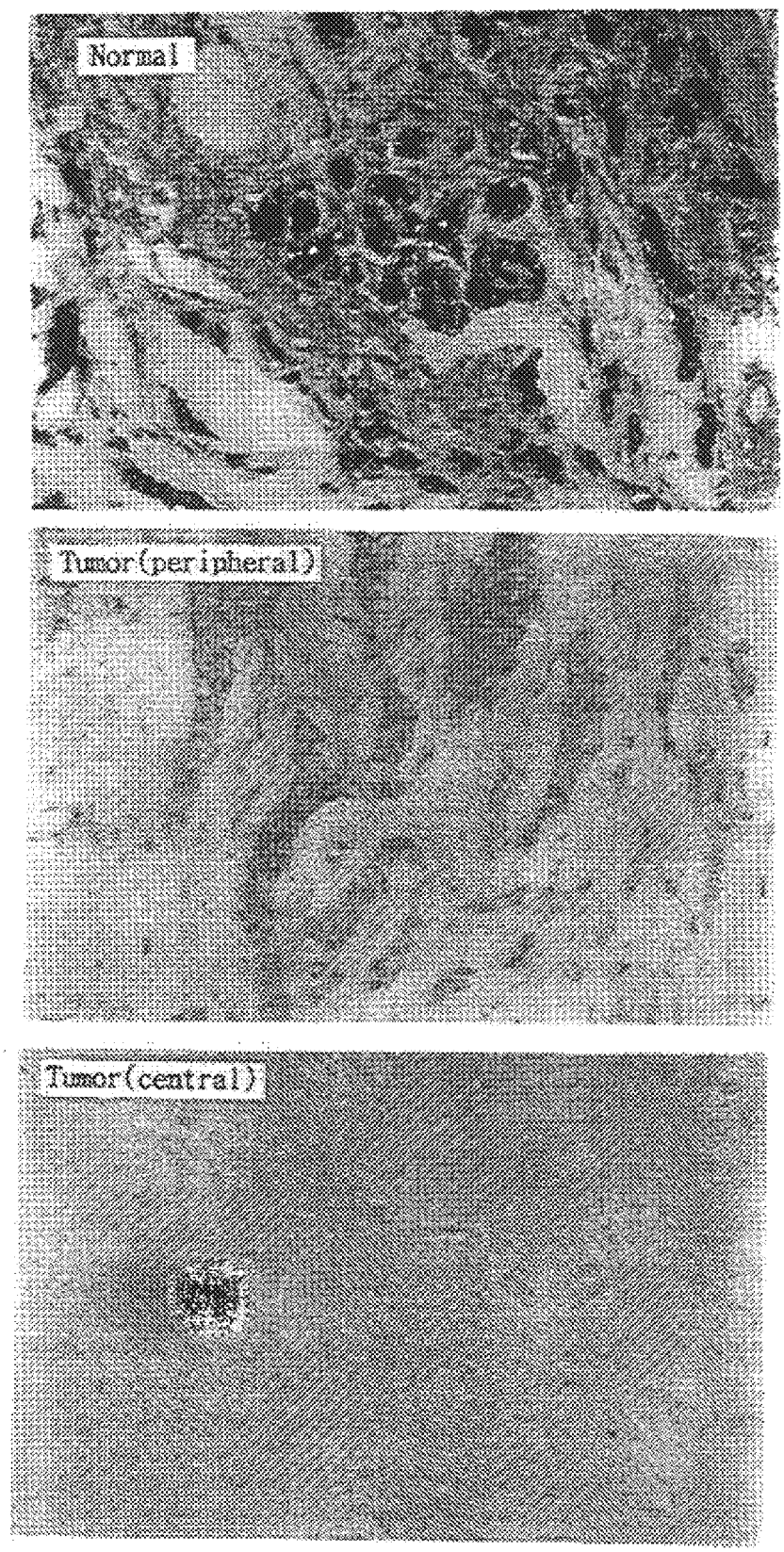
FIG. 4 is an in situ hybridization photograph showing the distribution of SYG972 in human breast cancer tissue.

Using in situ hybridization method as in Example 4, breast cancer cells from different patients were collected to investigate the expression of SYG972 mRNA. Results are shown in FIG. 4 and Table 2. SYG972 mRNA was scarcely observed in tumor cells whereas it was highly expressed in the surrounding normal cells. Especially among the cancer tissues, weak expression was observed at the boundary of cancer which adjacent to the normal cells, but SYG972 was not expressed in the center of the cancer tissue at all.

TABLE 2

| Type | Tissue site | Degree of expression |
|---|---|---|
| Carcinoma | Normal | ++ |
|  | Tumor exterior | − |
|  | Tumor (central) | − |
| Carcinoma | Normal | +++ |
|  | Tumor (exterior) | + |
|  | Tumor (central) | − |

TABLE 2-continued

| Type | Tissue site | Degree of expression |
|---|---|---|
| Carcinoma | Normal | +++ |
|  | Tumor (exterior) | ++ |
|  | Tumor (central) | − |
| Musinous Carcinoma | Normal | +++ |
|  | Tumor (exterior) | ++ |
|  | Tumor (central) | − |
| Carcinoma | Normal | +++ |
|  | Tumor (exterior) | ++ |
|  | Tumor (central) | + |
| Carcinoma | Normal | +++ |
|  | Tumor (exterior) | ++ |
|  | Tumor (central) | − |

EXAMPLE 6

Isolation of SYG972 Gene Genomic DNA

To isolate SYG972 gene genomic DNA from Lamda EMBL3 SP6/T7 human genome library (Clontech), $5 \times 10^6$ pfu phage was inoculated to K802 host bacteria and spread on 10 separate 150 mm petri-dishes. After observing bacterial lysis by phage, it was transferred on Nylon membrane, denatured according to the manufacturers' manual and cross-linked. A probe to screen SYG972 gene genomic DNA was obtained by marking total cDNA of SYG972 DNA gene with $\alpha$-$^{32}$P-[dCTP] by a random primer labeling method. The thusly prepared cDNA probe was hybridized by Southern blot hybridization, washed and exposed on x-ray film for 1 week to determine the existence of SYG972 genomic DNA. With 13 positive clones obtained from the first screening, $2^{nd}$ and $3^{rd}$ screening were performed using the same procedures finally obtaining a single clone containing 11 kb long insert. The obtained clone was cut by BamH I restriction enzyme, electrophoresed in 0.8% agarose gel to obtain 4 kb DNA fragment by performing Southern blot hybridization by using cDNA probe marked with radioisotope. The thusly obtained fragment was cloned into pUC19 plasmid vector, DNA sequenced to verify that it is SGY972 gene genomic DNA. DNA sequence of SYG972 gene is listed as Sequence No. 3.

SYG972 genomic DNA is composed of 4 exons and 3 introns, the sequence that connects exons coincides accurately with SYG972 cDNA sequence. The promoter comprises base No. 1 to base No. 2973. Exon 1 is base No. 2974 to base No. 3036, Exon 2 is base No. 3394 to base No. 3495, Exon 3 is base No. 3629 to base No. 3901, and Exon 4 is base No. 3929 to base No. 4444.

EXAMPLE 7

Determination of Activity of SYG972 (Gadd45-γ) Promoter

To determine the activity of SYG972 promoter, the promoter region was cloned into pGL-basic (Promega) vector. The Cloned promoter site starts ca. 80 bp upper segments of the protein synthesis signal (ATG codon) and has a 1.2 kb size towards the 5' direction. This vector was co-transferred with pRL-TK (Promega) vector into monkey kidney cell line, COS-7 cell line using LipofecAmine Plus (GibcoBRL). Twenty four hours after the transfer, cells were sonicated to obtained a protein extract. Using 20 μl of the extract, activities of Firefly luciferase and Renila luciferase were determined by using Luminometer. As a control group to determine SYG972 promoter activity, pGL-basic vector without promoter and pGL-control vector with SV40 promoter and enhancer were used. The error that can be caused by DNA transfer and amount of protein were calibrated with Renila luciferase activity.

Figure 5:
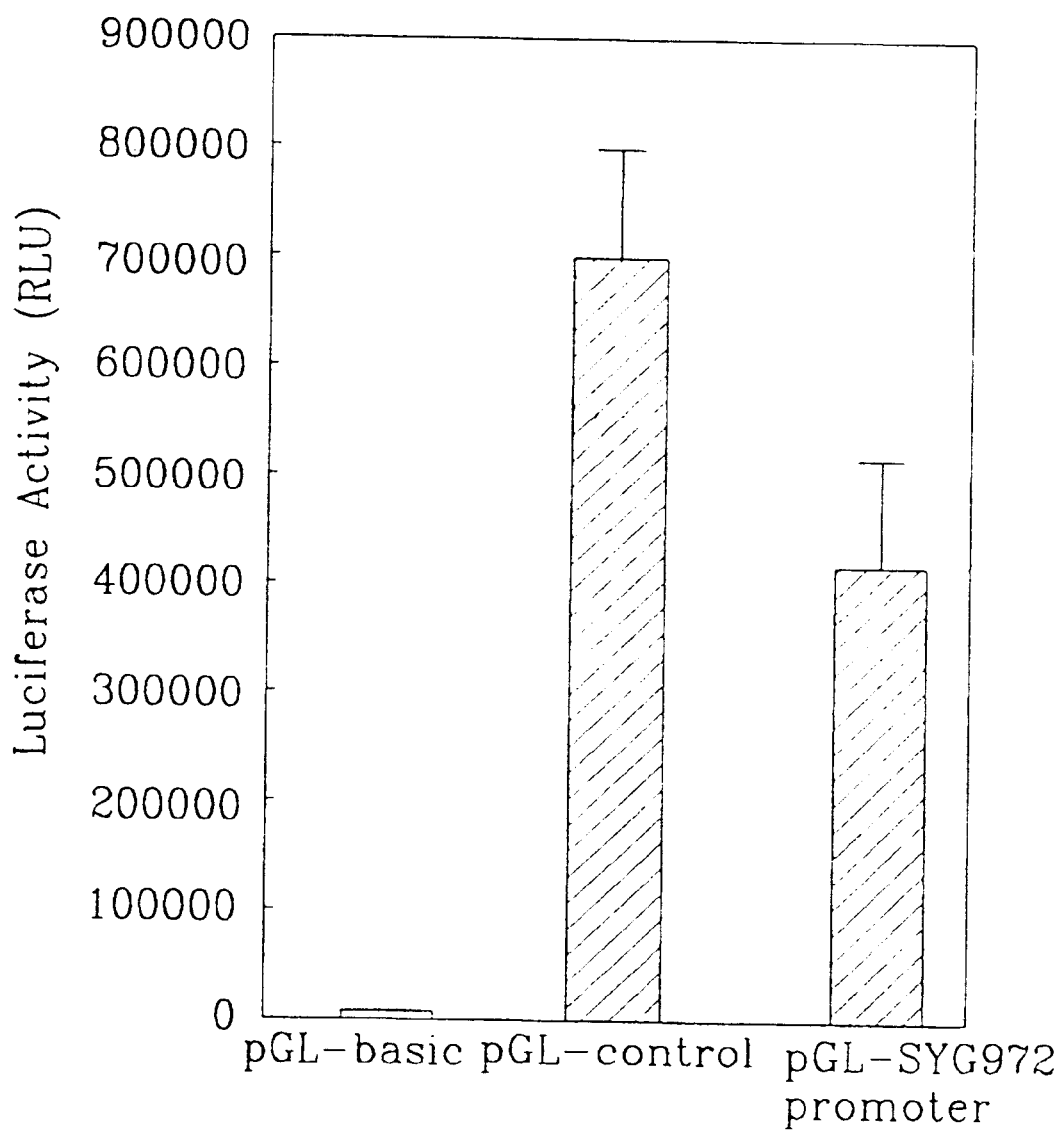
FIG. 5 is a graph showing a degree of activation of SYG972 promoter.

As shown in FIG. 5, SYG972 promoter has an activity as a promoter in monkey kidney cell line.

According to the present invention, SYG972 genomic DNA can be used in cancer diagnosis and treatment and in diagnosing cell differentiation related disease. Also the SYG972 gene promoter according to the present invention can be used in designing and screening drugs for cancer and degenerative nervous disease.

What is claimed is:

1. An isolated DNA comprising the nucleotide sequence of SEQ ID NO: 3.

2. An isolated DNA consisting of a fragment of SEQ ID NO: 3, wherein said fragment comprises nucleotides 1–2973, nucleotides 2974–3036, nucleotides 3394–3495, nucleotides 3629–3901 or nucleotides 3929–4444 of SEQ ID NO: 3.

* * * * *